United States Patent [19]

Kakumoto

[11] 4,431,961
[45] Feb. 14, 1984

[54] TURNABLE ELECTRODE

[75] Inventor: Michio Kakumoto, Naruto, Japan

[73] Assignee: Otsuka Pharmaceutical Factory, Inc., Tokushima, Japan

[21] Appl. No.: 301,225

[22] Filed: Sep. 11, 1981

[30] Foreign Application Priority Data

Sep. 16, 1980 [JP] Japan .................... 55-131784[U]

[51] Int. Cl.³ .................................. G01R 31/12
[52] U.S. Cl. ............................. 324/54; 209/527
[58] Field of Search ........... 209/522, 529, 527, 530; 324/54, 447; 73/864.82

[56] References Cited

U.S. PATENT DOCUMENTS

| | | | |
|---|---|---|---|
| 2,616,068 | 10/1952 | McDonald | 209/530 X |
| 3,684,089 | 8/1972 | McMeekin | 209/530 X |
| 4,125,805 | 11/1978 | Nagamatsu | . |
| 4,243,932 | 1/1981 | Kakumoto | . |

FOREIGN PATENT DOCUMENTS 48-45240  6/1973  Japan .
50-6998   3/1975  Japan .

*Primary Examiner*—Stanley T. Krawczewicz
*Assistant Examiner*—Jose M. Solis
*Attorney, Agent, or Firm*—Armstrong, Nikaido, Marmelstein & Kubovcik

[57] ABSTRACT

This invention relates to a turnable electrode which is positionable in contact or proximity with a specified portion of an article which is being transported, the electrode having in its periphery at least one access portion shaped in conformity with the contour of the specified portion of the article, the electrode being turnable as the article is transported forward to bring the access portion into contact or proximity with the specified portion of the article.

8 Claims, 5 Drawing Figures

TURNABLE ELECTRODE

BACKGROUND OF THE INVENTION

This invention relates to an electrode which is positionable in contact or proximity with a specified portion of an article which is being transported.

Plate-like, or lattice- or rake-shaped electrodes are usually used when there is a need to bring a specified portion of an article into contact with an electrode during the transport of the article, for example, when sealed containers made of electrically insulating material such as plastics or glass and having a parenteral solution, retorted food or like contents enclosed therein are checked for pinholes, cracks, etc. (hereinafter referred to collectively as "pinholes") by positioning the container between a pair of electrodes, impressing a voltage across the electrodes to produce a discharge current on the container and detecting the discharge current.

With reference to FIG. 5, such a plate-like, or lattice- or rake-shaped electrode Y has resiliency and is so arranged as to at least partially position in the path of transport of an article X, such that the article X in transport moves forward in contact with the electrode Y while pushing the electrode away against the resiliency of the electrode.

However, when the article X moves some distance, the electrode Y, with its restoring force, returns to its original vertical position out of contact with the article, with the result that the electrode fails to fully contact or gain access to a portion X' shown in FIG. 5 although the article has a simple shape. This tendency becomes more pronounced when the article has a complicated shape. Thus the electrode is not always capable of fully contacting or gaining access to the whole desired portion of the article whether continuously or simultaneously. Furthermore the electrode is subject to fatigue due to contact, friction or bending and therefore is not durable. When having a complicated shape or recess at the specified portion, the article involves a dead zone where the electrode is unable to contact or gain full access to the article. The conventional electrode has another drawback in that it is likely to mar and deteriorate the article if the article is made of soft plastics or like material.

When the electrode is used for checking sealed containers for pinholes by the above-mentioned method, the drawback of the electrode that it is incapable of fully contacting or gaining access to some desired portion of the container reduces the accuracy of checking. For example, if the article X shown in FIG. 5 has a pinhole at the portion X', the electrode is unable to contact or gain full access to the defective portion, failing to produce a discharge current sufficient for detecting the pinhole. Reduced checking accuracy similarly results from the drawback involving a dead zone.

The main object of this invention is to provide an electrode free of the foregoing problems.

SUMMARY OF THE INVENTION

This object can be fulfilled by a turnable electrode having in its periphery at least one access portion shaped in conformity with the contour of a specified portion of an article to be positioned in contact or proximity with the electrode at the specified portion while the article is being transported, the electrode being turnable as the article is transported forward to bring the access portion into contact or proximity with the specified portion of the article.

According to the invention, the access portion shaped in conformity with the contour of a specified portion of the article to be positioned for the electrode is positionable in contact or proximity with the specified portion as the electrode is turned with the transport of the article. Since the electrode is thus adapted to come into contact or proximity with every part of the specified portion of the article, the electrode assures improved accuracy when checking containers for pinholes, is less susceptible to fatigue due to friction, etc., and therefore has improved durability, and is less likely to permit occurrence of dead zones even when the specified portion of the article has a complicated shape or recess to ensure higher accuracy, for example, in detecting pinholes. Moreover the electrode involves a reduced likelihood of marring or otherwise deteriorating the article.

BRIEF DESCRIPTION OF THE DRAWINGS

The above object and other objects, features and advantages of the present invention will become apparent from the following description of embodiments of the invention with reference to the accompanying drawings, in which.

DETAILED DESCRIPTION OF THE INVENTION

The present invention will be described below as embodied for use in systems for checking sealed containers of polyethylene having a parenteral solution enclosed therein (hereinafter referred to merely as "containers") for pinholes.

Figure 1:
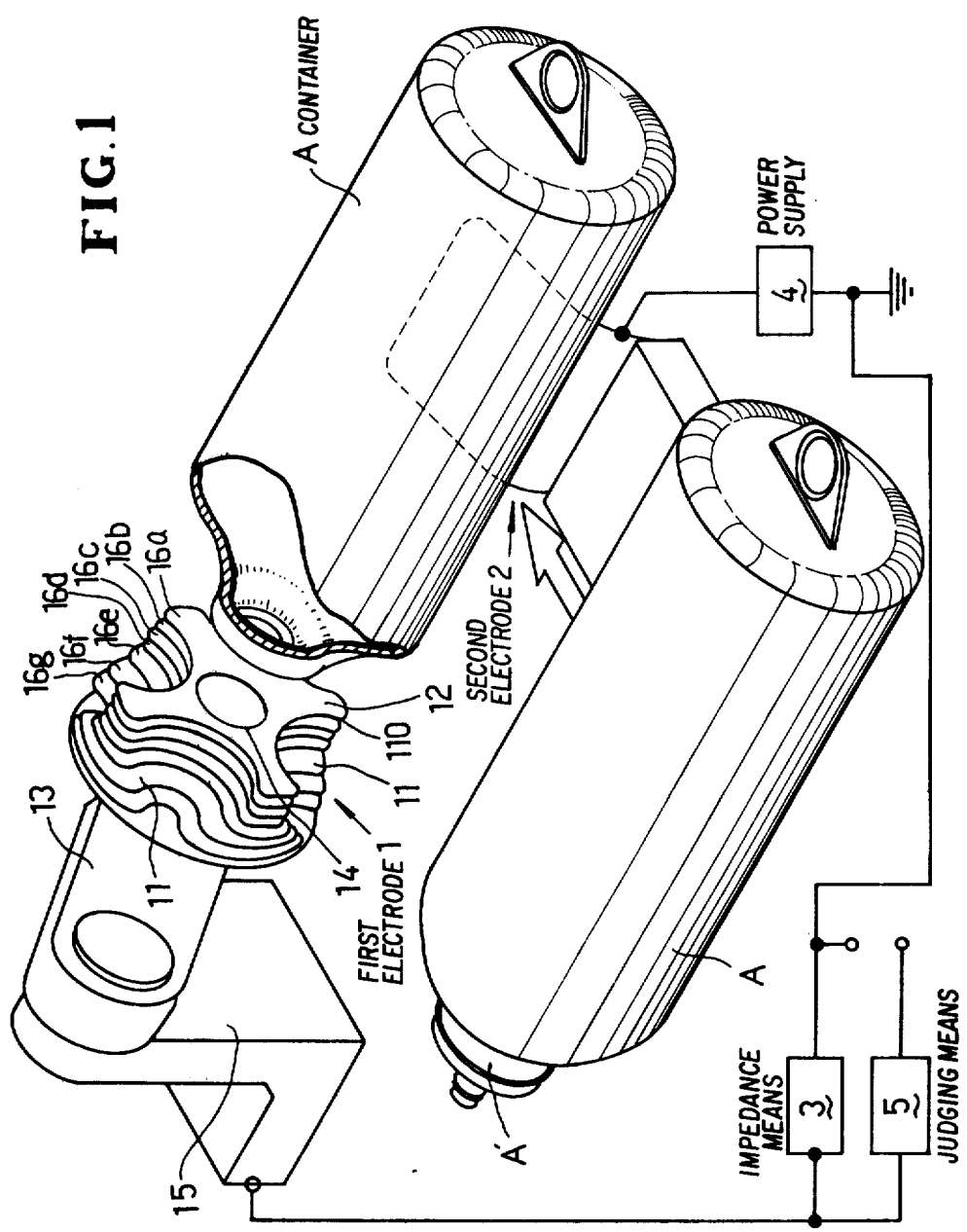
FIG. 1 is a schematic view showing a system of the single current type for checking containers for pinholes including an electrode embodying the invention.

FIG. 1 schematically shows a pinhole detecting system of the single current type.

The system has a first electrode 1 and a second electrode 2 which are positioned in the path of transport of containers A sent forward one by one on an unillustrated conveyor and adapted to come into contact with each container A. The more advanced (upper in the figure) container is partially broken away to more clearly show the configuration of the electrode 1. The electrode 1 is connected to one terminal of impedance means 3. An a.c. power supply 4 is connected between the electrode 2 and the other terminal of the impedance means 3. Judging means 5 is further connected to the impedance means 3. A terminal of the power supply 4 is grounded.

Figure 2:
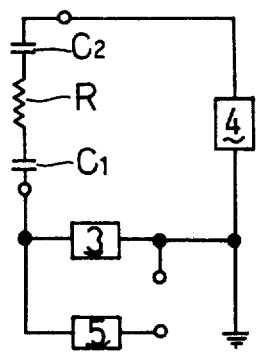
FIg. 2 is a diagram showing a circuit electrically equivalent to the system of FIG. 1.

The system of FIG. 1 can be interpreted as the electric circuit shown in FIG. 2, in which indicated at C1 is the electrostatic capacitance between the electrode 1 and the contents of the container A, at C2 the capacitance between the electrode 2 and the contents, and at R is the electric resistance of the contents.

When a voltage is applied across the electrodes 1 and 2, a corona discharge current $i_1$ flows between the electrodes if the container A has no pinhole, or a spark discharge current $i_2$ flows between the electrodes if the container A has a pinhole. Since there is the relation of $i_2 > i_1$, a threshold value $i_s$ (definite reference value) having the relation of $i_2 > i_s > i_1$ is predetermined, such that if the discharge current detected across the electrodes for the container A is greater than $i_s$, the result indicates the pesence of a pinhole, whereas if it is smaller than $i_s$, the container is accepted as having no pinhole.

Figure 3:
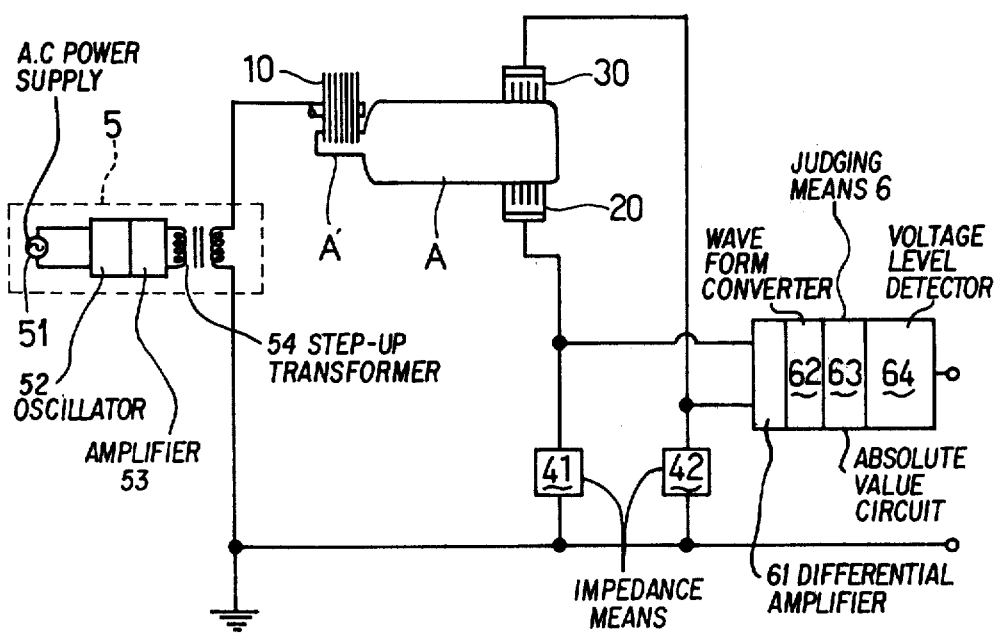
FIG. 3 is a diagram showing a system of the differential type for checking containers for pinholes including an electrode embodying the invention.

FIG. 3 schematically shows a system of the differential type for detecting pinholes.

The system includes a first electrode 10 and two second electrodes 20, 30 which are positioned in the path of transport of containers A sent forward one by one by an unillustrated conveyor and adapted to come into contact with each container A.

The second electrodes 20, 30 are at approximately equal distances from the first electrode 10. The second electrode 20 is connected to one terminal of first impedance means 41, while the other second electrode 30 is connected to one terminal of second impedance means 42 disposed in parallel to the first impedance means 41. An a.c. power supply unit 5 is provided with a step-up transformer 54 the secondary winding of which is connected between the first electrode 10 and the other terminals of the impendance means 41, 42. These other terminals of the impedance means 41, 42 are grounded to assure safety. The power supply unit 5 comprises an a.c. power supply 51, an oscillator 52 for producing the desired alternating wave form from the output of the power supply 51 (and also for altering the frequency of the power supply output), an amplifier 53 for amplifying the output from the oscillator 52, and the step-up transformer 54 for producing in its secondary winding the desired high voltage from the amplifier output. Thus the power supply unit 5 produces from any low voltage and any low-frequency wave the desired high voltage and desired high-frequency wave in the secondary winding of the transformer 54. For detecting pinholes in containers A, the system includes judging means 6 which individually detects two discharge currents on the container A, i.e. the current flowing between the electrodes 10 and 20 and the current flowing between the electrodes 10 and 30, and converts the difference between the currents to the difference between the voltages across the terminals of the impedance means 41 and 42. The judging means 6 comprises a differential amplifier 61 connected to the electrodes 20, 30, a wave form converter circuit 62 for taking out only the wave forms higher than a preset level from the output of the amplifier 61, an absolute value circuit 63 for arranging the output waves of the circuit 62 in the positive or negative direction, and a comparator (voltage level detector) 64 connected to the circuit 63.

Figure 4:
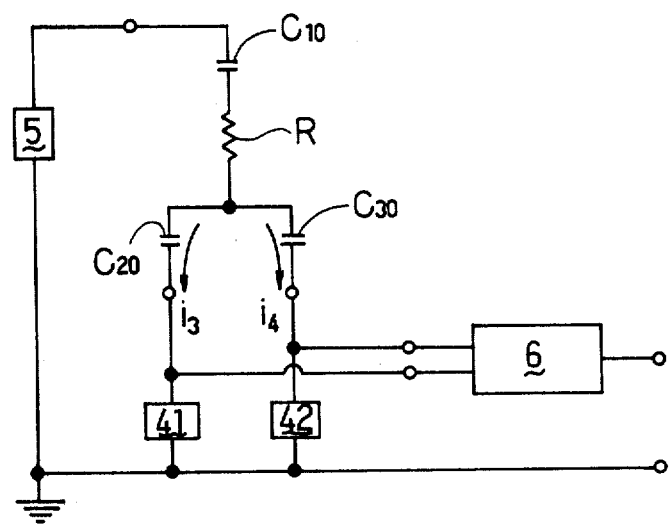
FIG. 4 is a diagram showing a circuit electrically equivalent to the system of FIG. 3.
Figure 5:
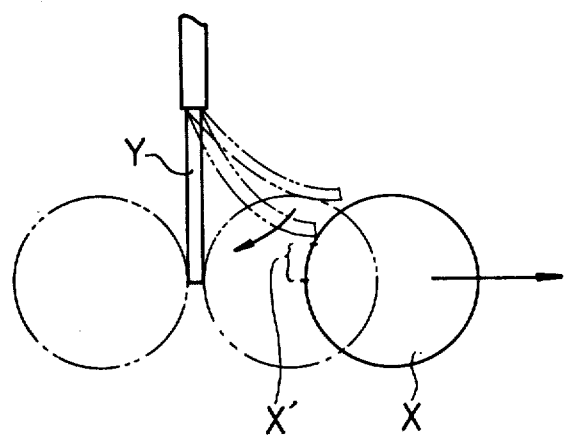
FIG. 5 is a diagram showing a conventional electrode and an article in contact or proximity therewith.

The system of the differential type shown in FIG. 3 can be interpreted as being electrically equivalent to the circuit of FIG. 4.

With reference to FIG. 4, indicated at C10 is the capacitance between the electrode 10 and the contents of the container A, at C20 the capacitance between the electrode 20 and the contents, at C30 the capacitance between the electrode 30 and the contents, and at R the electric resistance of the contents.

In the equivalent circuit, the impedance of the closed circuit of: electrode 10-container A-electrode 20-impedance means 41-power supply unit 5-electrode 10 is made substantially equal to the impedance of the closed circuit of: electrode 10-container A-electrode 30-impedance means 42-power supply unit 5-electrode 10. The impedance means 41 is equivalent to the impedance means 42. The capacitance C20 is rendered substantially equal to the capacitance C30. The impedances of the means 41, 42 are so small as to be negligible relative to the impedances C10, C20, C30 and resistance R.

When a voltage is applied across the electrode 10 and the electrodes 20, 30, two corona discharge currents $i_3$, $i_4$ are produced on the container A as seen in FIG. 4 if the container has no pinhole. The difference between the currents is substantially zero or nearly zero.

If the container A has a pinhole, one of the two discharge currents is a spark discharge current, with an increased difference between the two discharge currents.

The judging means 6 detects the two discharge currents and converts the difference therebetween to a voltage value. The converted value indicates the absence of pinholes if it is zero or almost zero, or the presence of a pinhole if it is great. Alternatively the converted value indicates the absence of pinholes if it is smaller than a preset threshold value, or the presence of a pinhole if greater than the threshold value.

Whether the system is of the single current type or of the differential type, a d.c. voltage is usable instead of the a.c. voltage, in which case the speed at which the container travels between the electrodes must be suitably determined relative to the time constant RC (wherein C is a combined capacitance) inherent in the container. While the contents of the container must have some conductivity, the system operates satisfactorily when the resistance of the contents is sufficiently low relative to the insulation resistance of the container.

With either of the systems described above, the number and position of the second electrodes are suitably variable.

Embodiments of this invention are used as the first electrodes 1, 10 for the pinhole detecting systems described above.

The first electrode 10 included in the system of the differential type has the same construction as the first electrode 1 shown in FIG. 1.

The electrode 1 has in its periphery 12 a plurality of access portions 11 shaped in conformity with the contour of the mouth portion (specified portion) A' of the container A to be brought into contact with the electrode. The electrode 1 is rotatably supported by a shaft 14 on an arm 13, which in turn is turnably supported by a fixed frame 15. The electrode is always biased by unillustrated spring means so as to be positioned in the path of transport of the container A for contact therewith. The access portions 11 of the electrode are slightly enlarged and smoothly curved at their inlets 110 to permit the container A to come into contact therewith smoothly.

Containers A sent forward one after another by an unillustrated conveyor come into contact with one of the access portions 11 of the electrode, each at its mouth portion A', whereupon the container starts to turn the electrode against the action of the spring means while slightly lifting the electrode.

By virtue of the travel of the container A and resulting turn of the electrode, the container mouth portion A' properly comes into full fitting contact with the access portion 11, with the result that if the mouth portion A' has a pinhole, a discharge current is reliably produced which is sufficient for the detection of the pinhole. The container thereafter leaves the electrode. When one container A leaves the electrode, the next access portion 11 is located at the position where the next container A comes into contact with that access portion 11.

Although the system shown in FIGS. 1 and 3 has one first electrode according to the invention, a pair of such electrodes may be arranged as opposed to each other so that the mouth portion A' of the container A may be surrounded by access portions in contact therewith.

The electrode of this invention shown in FIG. 1 comprises a plurality of plate-like electrode elements 16a, 16b, 16c, . . . 16g which are arranged side by side longitudinally of the shaft 14, with or without a space formed therebetween. Each of the elements has parts of the access portions 11. When having this construction, the electrode can be fabricated merely by preparing the elements by simple press work and arranging the elements side by side, so that the electrode can be made easily with the access portions shaped in conformity with the contour of the specified portion of the article to be contacted with the electrode.

Instead of assembling the electrode from plate-shaped elements, the electrode may be made originally in the form of an integral piece.

Although the electrode of the invention shown in FIG. 1 is made turnable by the travel of the container A, the electrode may be turned, for example, by unillustrated suitable drive means in timed relation to the speed of travel of the container A. In this case, the electrode may be operable with only one access portion 11.

Electrodes according to the invention are used as the first electrodes 1, 10 in the systems shown in FIGS. 1 and 3 because with the container A made of synthetic resin, pinholes are likely to occur chiefly in the mouth portion A' thereof which has a complicated construction. When desired, the electrode of this invention is usable as a second electrode in place of the plate-like electrode 2 in FIG. 1 or the lattice-shaped electrodes 20, 30 shown in FIG. 3.

The electrode of this invention is made from copper or some other material suitable for electrodes.

Although the electrodes used in the illustrated pinhole detecting systems are adapted for contact with the container A, such electrodes need not always be made positionable in contact with the container but may be positioned in proximity with the container to perform the desired function.

I claim:

1. An electrode for checking the integrity of an article being transported on a moving conveyor comprising:
   an element rotatably supported on an axis transverse to the direction of movement of said conveyor, said element having formed in its periphery at least one access portion shaped to conform substantially to the exterior contour of said article, said axis being positioned adjacent the path of movement of said article on said conveyor whereby the exterior of said article passes in close proximity with said conforming access portion and rotation of said electrode about said axis maintains said access portion in close proximity with said article.

2. An electrode for checking the integrity of an article being transported on a moving conveyor comprising:
   a contact element rotatably supported on an axis transverse to the direction of movement of said conveyor, said contact element having formed in its periphery a plurality of access portions shaped to conform to the exterior contour of said article, said axis being positioned adjacent the path of travel of said article and being biased to bring said access portions into said path whereby the exterior of said article will engage one of said conforming access portions and movement of said article will cause said electrode to rotate about said axis and maintain said exterior contour in close proximity with said access portion.

3. An electrode as claimed in claim 2, wherein said electrode comprises a plurality of plate-like elements arranged side by side and each being formed to conform to a corresponding portion of the exterior contour of said article.

4. An electrode as claimed in claim 3, wherein said plate-like elements are in contact with each other.

5. An electrode as claimed in claim 3, wherein said plate-like elements are spaced from each other.

6. A turnable electrode for use in checking for pinholes in a sealed container of electrical insulating material having contained therein an electrically conductive fluid, said container being transported between said turnable electrode and a second electrode, said electrodes having impressed thereacross a voltage sufficient to generate a discharge current,
   said turnable electrode having formed in its periphery at least one access portion shaped to conform with the contour of a portion of said container and being mounted to turn about an axis transverse to the path of transport of said container,
   said electrode being disposed so that said container will engage said access portion in close enough proximity to permit the generation of a discharge current, said electrode turning about said axis to permit the transport of said container without disruption.

7. A turnable electrode as claimed in claim 6, wherein said electrode comprises a plurality of plate-like elements arranged side by side, each element having a part of said access portion therein, said elements being in contact with each other.

8. A turnable electrode as claimed in claim 6, wherein said electrode comprises a plurality of plate-like elements, each element having a part of said access portion therein, said elements being arranged side by side and spaced from each other along said axis.

* * * * *